US009907794B2

(12) United States Patent
Fujihara

(10) Patent No.: US 9,907,794 B2
(45) Date of Patent: *Mar. 6, 2018

(54) PHARMACEUTICAL COMPOSITION

(71) Applicant: SUMITOMO DAINIPPON PHARMA CO., LTD, Osaka (JP)

(72) Inventor: Kazuyuki Fujihara, Suzuka (JP)

(73) Assignee: SUMITOMO DAINIPPON PHARMA CO., LTD, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/733,204

(22) Filed: Jun. 8, 2015

(65) Prior Publication Data
US 2015/0265611 A1 Sep. 24, 2015

Related U.S. Application Data

(63) Continuation of application No. 14/512,189, filed on Oct. 10, 2014, which is a continuation of application No. 14/183,283, filed on Feb. 18, 2014, now Pat. No. 8,883,794, which is a continuation of application No. 11/919,678, filed as application No. PCT/JP2006/310571 on May 26, 2006, now Pat. No. 8,729,085.

(30) Foreign Application Priority Data

May 26, 2005 (JP) .................. 2005-153508

(51) Int. Cl.
*A61K 31/496* (2006.01)
*A61K 9/20* (2006.01)
*A61K 9/00* (2006.01)
*C07D 417/12* (2006.01)

(52) U.S. Cl.
CPC .......... *A61K 31/496* (2013.01); *A61K 9/0053* (2013.01); *A61K 9/2009* (2013.01); *A61K 9/2018* (2013.01); *A61K 9/2027* (2013.01); *A61K 9/2031* (2013.01); *A61K 9/2054* (2013.01); *A61K 9/2059* (2013.01); *A61K 9/2095* (2013.01); *C07D 417/12* (2013.01)

(58) Field of Classification Search
CPC .. A61K 31/496; A61K 9/0053; A61K 9/2009; A61K 9/2018; A61K 9/2027; A61K 9/2031; A61K 9/2054; A61K 9/2059; A61K 9/2095; A61K 9/2017; C07D 417/12
See application file for complete search history.

(56) References Cited

U.S. PATENT DOCUMENTS

| | | | |
|---|---|---|---|
| 4,551,177 A | 11/1985 | Trubiano et al. | |
| 4,600,579 A | 7/1986 | Salpekar et al. | |
| 4,609,675 A | 9/1986 | Franz | |
| 4,837,031 A | 6/1989 | Denton | |
| 4,911,921 A | 3/1990 | Denton et al. | |
| 5,047,246 A | 9/1991 | Gallian et al. | |
| 5,104,648 A | 4/1992 | Denton et al. | |
| 5,532,372 A | 7/1996 | Saji et al. | |
| 5,605,889 A | 2/1997 | Curatolo et al. | |
| 6,150,366 A | 11/2000 | Arenson et al. | |
| 6,586,617 B1 | 7/2003 | Tabuchi et al. | |
| 7,141,249 B2 | 11/2006 | Ohashi et al. | |
| 7,727,553 B2 | 6/2010 | Fujihara | |
| 8,729,085 B2 | 5/2014 | Fujihara | |
| 8,883,794 B2 | 11/2014 | Fujihara | |
| 9,555,027 B2 | 1/2017 | Fujihara | |
| 2003/0203020 A1 | 10/2003 | Ortyl et al. | |
| 2004/0028741 A1 | 2/2004 | Fujihara | |
| 2004/0186105 A1 | 9/2004 | Allenspach et al. | |
| 2005/0147669 A1 | 7/2005 | Lawrence et al. | |
| 2006/0204486 A1 | 9/2006 | Pyke et al. | |

FOREIGN PATENT DOCUMENTS

| | | | |
|---|---|---|---|
| EP | 1 327 440 | 7/2003 | |
| EP | 1327440 A1 | 7/2003 | |
| EP | 1 371 646 | 12/2003 | |
| EP | 1 695 699 | 8/2006 | |
| JP | 08-325146 | 12/1996 | |
| JP | 2000-26292 | 1/2000 | |
| WO | WO 01/76557 A1 | 10/2001 | |
| WO | WO 02/24166 A1 | 3/2002 | |
| WO | WO 03/090720 A1 | 11/2003 | |
| WO | WO 2004/017973 | 3/2004 | |
| WO | WO 2004/017973 A1 | 3/2004 | |
| WO | WO 2004017973 A1 * | 3/2004 | ........... A61K 31/496 |
| WO | WO 2004/078173 A1 | 9/2004 | |

OTHER PUBLICATIONS

Gohil, Usha C. et al., "Investigations into the use of pregelatinised starch to deveop powder-filled hard capsules," International Journal of Pharmaceutics 285 (2004) pp. 51-63.
Request for Invalidation from invalidity proceedings in corresponding Chinese Application No. 200680018223.4 (original Chinese version and English-language translation), Aug. 5, 2012.
Bi Dianzhou, Pharmaceutics, Edition 4, Beijing: People's Medical Publishing House, Feb. 2003.
"Application and Effect of Pregelatinized Starch in Tablets," Chinese Pharmaceutical Information, vol. 16, Issue 7, 2000, published in 2000.

(Continued)

Primary Examiner — Sarah Pihonak
(74) Attorney, Agent, or Firm — Oblon, McClelland, Maier & Neustadt, L.L.P.

(57) ABSTRACT

A preparation for oral administration comprising: a pregelatinized starch comprising N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]-heptanedicarboxyimide hydrochloride (lurasidone) represented by the formula (1) as an active ingredient; a water-soluble excipient; and a water-soluble polymeric binder, the preparation exhibiting an invariant level of elution behavior even when the content of its active ingredient is varied.

30 Claims, 3 Drawing Sheets

(56) References Cited

OTHER PUBLICATIONS

"Use of Pregelatinized Starch in Tablet Manufacturing," Chinese Pharmaceutical Journal, vol. 29, Issue 4, Apr. 1994, published in Apr. 1994.
"Application of the Pregelatinized Starch in Capsules," Chinese Journal of Modern Applied Pharmacy, vol. 8, Issue 1, Feb. 1991, published in Feb. 1991.
"In Vitro Dissolution and Bioavailability of Acyclovir Capsules Formulated with Pregelatinized Starch," Chinese Journal of Pharmaceuticals, 1998, 29(5), published on May 20, 1998.
Dissolution of Drug Solid Preparation, "Factors Influencing Dissolution Rates," Wu Guangchen, Yue Zhiwei, People's Medical Publishing House, published in Oct. 1994.
Reply Brief from invalidity proceedings in corresponding Chinese Application.
No. 200680018223.4 (original Chinese version and English-language translation), Oct. 25, 2012.
Examination Decision on the Request for Invalidation in corresponding Chinese Application No. 200680018223.4 (original Chinese version and English-language translation), Apr. 26, 2013.
EPO Communication dated Feb. 1, 2012, with enclosed Supplemental Search Report, in EPO Appln. 11181100.6.
Kibbe, Handbook of Pharmaceutical Excipients, Chapter 7, pp. 528-530 (2000).
Handbook of Pharmaceutical Excipients, 2nd edition, vol. 491, The Pharmaceutical Press, 1994.
Chueshov, V. 1., et al., "Manufacturing Technologies of Drugs," Promyshlennaya Technologiya Lekarstv, vol. 2, pp. 10-11 (1999). Russian Official Action (dated 2009).
Makino, T., et al., "Importance of Gelatinization Degree of Starch Past Binder in Hardness and Disintegration Time of Tablets," Chem. Pharm. Bull., vol. 43, No. 3, pp. 514-116 (1995).
Ghosh, Tapash K. et al., "Theory and Practice of Contemporary Pharmaceutics," CRC Press, Chapter 10, p. 279-331 (2005).
Gennaro, Alfonso R., "Remington: The Science and Practice of Pharmacy," 19$^{th}$ Edition, Mack Publishing Co., Chapter 92, vol. II, pp. 1615-1620, [1995].
Petition for Inter Partes Review of U.S. Pat. No. 9,555,027, filed Apr. 18, 2017 in IPR 2017-01292 (Terminated).
Exhibit 1001 in IPR 2017-01292 filed Apr. 18, 2017 (Terminated) U.S. Pat. No. 9,555,027 B2, issued Jan. 31, 2017, 18 pages.
Exhibit 1002 in IPR 2017-01292 filed Apr. 18, 2017 (Terminated) Declaration of Graham Buckton Final Declaration, 142 pages.
Exhibit 1003 in IPR 2017-01292 filed Apr. 18, 2017 (Terminated) Graham Buckton Curriculum Vitae, 45 pages.
Exhibit 1004 in IPR 2017-01292 filed Apr. 18, 2017 (Terminated) Declaration of Scott Bennett, 266 pages.
Exhibit 1005 in IPR 2017-01292 filed Apr. 18, 2017 (Terminated) Scott Bennett Curriculum Vitae, 7 pages.
Exhibit 1006 in IPR 2017-01292 filed Apr. 18, 2017 (Terminated) Declaration of Adam Kaplin, 15 pages.
Exhibit 1007 in IPR 2017-01292 filed Apr. 18, 2017 (Terminated) Adam Kaplin Curriculum Vitae, 9 pages.
Exhibit 1008 in IPR 2017-01292 filed Apr. 18, 2017 (Terminated) European Patent Application Publication No. EP 1 327 440 A1, Published Jul. 16, 2003, 32 pages.
Exhibit 1009 in IPR 2017-01292 filed Apr. 18, 2017 (Terminated) M. Aulton, "Pharmaceutics: The Science of Dosage Form Design", Churchill Livingstone, 1988, 113 pages.
Exhibit 1010 in IPR 2017-01292 filed Apr. 18, 2017 (Terminated) U.S. Pat. No. 4,911,921, Issued Mar. 27, 1990, 4 pages.
Exhibit 1011 in IPR 2017-01292 filed Apr. 18, 2017 (Terminated) K.P.R. Chowdary et al., "Formulation and Evaluation of Dispersible Tablets with Pregelatinized Starch", Indian Drugs, 35(6), Jun. 1998, 4 pages.
Exhibit 1012 in IPR 2017-01292 filed Apr. 18, 2017 (Terminated) WIPO Publication No. WO2004/017973 A1, Published Apr. 3, 2004, 18 pages.
Exhibit 1013 in IPR 2017-01292 filed Apr. 18, 2017 (Terminated) File History of U.S. Pat. No. 9,555,027, 373 pages.

Exhibit 1014 in IPR 2017-01292 filed Apr. 18, 2017 (Terminated) U.S. Pat. No. 8,729,085, Issued May 20, 2014, 20 pages.
Exhibit 1015 in IPR 2017-01292 filed Apr. 18, 2017 (Terminated) File History of U.S. Pat. No. 8,729,085, 633 pages
Exhibit 1016 in IPR 2017-01292 filed Apr. 18, 2017 (Terminated) M. Bell et al., "The Positive and Negative Syndrome Scale and the Brief Psychiatric Rating Scale Reliability, Compatibility, and Predictive Validity", The Journal of Nervous and Mental Disease, 1992, 6 pages.
Exhibit 1017 in IPR 2017-01292 filed Apr. 18, 2017 (Terminated) Fujihara map of examples—with 027, Apr. 18, 2017, 1 page.
Exhibit 1018 in IPR 2017-01292 filed Apr. 18, 2017 (Terminated) "Guidance for Industry Bioavailability and Bioequivalence Studies for Orally Administered Drug Products—General Considerations", U.S. Department of Health and Human Services Food and Drug Administration Center for Drug Evaluation and Research (CDER), 2003, 26 pages.
Exhibit 1019 in IPR 2017-01292 filed Apr. 18, 2017 (Terminated) WIPO Publication No. WO2004/017973A1, Published Mar. 4, 2004, 23 pages.
Exhibit 1020 in IPR 2017-01292 filed Apr. 18, 2017 (Terminated) D. Becker et al., "Effectiveness of Binders in Wet Granulation: A Comparison Using Model Formulations of Different Tabletability", Drug Development and Industrial Pharmacy, 23(8), 791-808 (1997), 18 pages.
Exhibit 1021 in IPR 2017-01292 filed Apr. 18, 2017 (Terminated) "Handbook of Pharmaceutical Excipients" (excerpted), Pharmaceutical Press, 2003. 50 pages.
Exhibit 1022 in IPR 2017-01292 filed Apr. 18, 2017 (Terminated) "Handbook of Pharmaceutical Granulation Technology", Marcel Dekker. Inc., 17 pages.
Exhibit 1023 in IPR 2017-01292 filed Apr. 18, 2017 (Terminated) U.S. Patent Publication No. 2004/0186105 A1, Published Sep. 23, 2004, 15 pages.
Exhibit 1024 in IPR 2017-01292 filed Apr. 18, 2017 (Terminated) European Patent Application Publication No. EP 1 371 646 A1, Published Dec. 17, 2003, 75 pages.
Exhibit 1025 in IPR 2017-01292 filed Apr. 18, 2017 (Terminated) "Starch 1500" Brochure, Colorcon, Copyright 1999, 6 pages.
Exhibit 1026 in IPR 2017-01292 filed Apr. 18, 2017 (Terminated) M. Keller, "Improving the Course fo Illness and Promoting Continuation of Treatment of Bipolar Disorder", J. Clin. Psychiatry, 2004;65 (suppl 15), 5 pages.
Exhibit 1027 in IPR 2017-01292 filed Apr. 18, 2017 (Terminated) Kottke et al., "Tablet Dosge Forms", Modern Pharmaceutics, 2002, 49 pages.
Exhibit 1028 in IPR 2017-01292 filed Apr. 18, 2017 (Terminated) R. Shangraw et al., "A Survey of Current industrial Practices in the Formulation and Manufacture of Tablets and Capsules", Pharmaceutical Technology, 1993, 15 pages.
Exhibit 1029 in IPR 2017-01292 filed Apr. 18, 2017 (Terminated) J.B. Schwartz et al., "Intragranular Starch: Comparison of Starch USP and Modified Cornstarch", Journal of Pharmaceutical Sciences, vol. 64, No. 2, 1975, 5 pages.
Exhibit 1030 in IPR 2017-01292 filed Apr. 18, 2017 (Terminated) C. R. Cunningham et al., "Evaluation of a Partially Pregelatized Starch in Comparison with Superdisintegrants in a Direct-Compression Hydrochlorothiazide Formulation", Colorcon, 1999, 6 pages.
Exhibit 1031 in IPR 2017-01292 filed Apr. 18, 2017 (Terminated) U.S. Pat. No. 4,600,579, Issued Jul. 15, 1986, 8 pages.
Exhibit 1032 in IPR 2017-01292 filed Apr. 18, 2017 (Terminated) U.S. Pat. No. 4,837,031, Issued Jun. 6, 1989, 6 pages.
Exhibit 1033 in IPR 2017-01292 filed Apr. 18, 2017 (Terminated) U.S. Pat. No. 6,150,366, Issued Nov. 21, 2000, 7 pages.
Exhibit 1034 in IPR 2017-01292 filed Apr. 18, 2017 (Terminated) D. R. Vanderpoel et al., "Adherence to a Fixed-Dose Combination of Resiglitazone Maleate/Metformin Hydrochloride in Subjects with Type 2 Diabetes Mellitus: A Retrospective Database Analysis", Clinical Therapeutics, 2004, 10 pages.
Exhibit 1035 in IPR 2017-01292 filed Apr. 18, 2017 (Terminated) U.S. Pat. No. 5,605,889, Issued Feb. 25. 1997, 17 pages.

(56) References Cited

OTHER PUBLICATIONS

Exhibit 1036 in IPR 2017-01292 filed Apr. 18, 2017 (Terminated) European Patent Application Publication No. EP 1 695 699 A1, Published Aug. 30, 2006, 32 pages.
Exhibit 1037 in IPR 2017-01292 filed Apr. 18, 2017 (Terminated) U.S. Pat. No. 6,586,617, Issued Jul. 1, 2003, 62 pages.
Exhibit 1038 in IPR 2017-01292 filed Apr. 18, 2017 (Terminated) U.S. Pat. No. 7,141,249, Issued Nov. 28, 2006, 7 pages.
Exhibit 1039 in IPR 2017-01292 filed Apr. 18, 2017 (Terminated) U.S. Patent Application Publication No. 2004/0028741, Published Feb. 12, 2004, 19 pages.
Exhibit 1040 in IPR 2017-01292 filed Apr. 18, 2017 (Terminated) U.S. Pat. No. 8,883,794 patent, Issued Nov. 11, 2014, 18 pages.
Exhibit 1041 in IPR 2017-01292 filed Apr. 18, 2017 (Terminated) File History of U.S. Pat. No. 8,883,794, 204 pages.
Exhibit 1042 in IPR 2017-01292 filed Apr. 18, 2017 (Terminated) "Pharmaceutical Preformulation and Formulation A Practical Guide from Candidate Drug Selection to Commercial Dosage Form", Taylor & Francis, 2001 CRC Press, 82 pages.
Exhibit 1043 in IPR 2017-01292 filed Apr. 18, 2017 (Terminated) V. P. Shah et al., "In Vitro Dissolution Profile Comparison—Statistics and Analysis of the Similarity Factor, $f_2$", Pharmaceutical Research, vol. 15, No. 6. 1998, 8 pages.
Exhibit 1044 in IPR 2017-01292 filed Apr. 18, 2017 (Terminated) M. Levina et al., "The Influence of Excipients on Drug Release from Hydroxypropyl Methylcellulose Matrices", Journal of Pharmaceutical Sciences, vol. 93, No. 11, Nov. 2004, 9 pages.
Exhibit 1045 in IPR 2017-01292 filed Apr. 18, 2017 (Terminated) Wu et al., "Predicting Drug Disposition via Application of BCS: Transport/Absorption/Elimination Interplay and Development of a Biopharmaceutics Drug Disposition Classification System", Pharmaceutical Research, vol. 22, No. 1, Jan. 2005, 13 pages.
Exhibit 1046 in IPR 2017-01292 filed Apr. 18, 2017 (Terminated) "British Pharmacopoeia 2001", 54 pages.
Exhibit 1047 in IPR 2017-01292 filed Apr. 18, 2017 (Terminated) 21 CFR 320.22, 3 pages.
Exhibit 1048 in IPR 2017-01292 filed Apr. 18, 2017 (Terminated) P. M. Hadadd et al., "Nonadherence with antiphychotic medication in schizophrenia: challenges and management strategies", Patient Related Outcome Measures 2014:5 43-62, 20 pages.
Exhibit 1049 in IPR 2017-01292 filed Apr. 18, 2017 (Terminated) U.S. Pat. No. 5,047,246, Issued Sep. 10, 1991, 16 pages.
Exhibit 1050 in IPR 2017-01292 filed Apr. 18, 2017 (Terminated) R.H. Chapman et al., "Predictors of Adherence With Antihypertensive and Lipid-Lowering Therapy", Arch Intern Med, vol. 165, May 23, 2005, 6 pages.
Exhibit 1051 in IPR 2017-01292 filed Apr. 18, 2017 (Terminated) Acetaminophen, Drugbank, Apr. 18, 2017, 46 pages.
Exhibit 1052 in IPR 2017-01292 filed Apr. 18, 2017 (Terminated) W.M. Greenberg et al., "Pharmacokinetics and Pharmacodynamics of Lurasidone Hydrochloride, a Second-Generation Antipsychotic: A Systematic Review of the Published Literature", Clin Pharmacokinet, 2016, 11 pages.
Exhibit 1053 in IPR 2017-01292 filed Apr. 18, 2017 (Terminated) Vaidecoxib, Drugbank, 11 pages.
Exhibit 1054 in IPR 2017-01292 filed Apr. 18, 2017 (Terminated) "USP 28 NF 23 The United States Pharmacopeia The National Formulary" United States Pharmacopeial Convention. Inc., 2005, 17 pages.
Exhibit 1055 in IPR 2017-01292 filed Apr. 18, 2017 (Terminated) Norfloxacin, U. S. National Library of Medicine National Center for Biotechnology Inforamtion Open Chemistry Database, 11 pages.

Exhibit 1056 in IPR 2017-01292 filed Apr. 18, 2017 (Terminated) "Orange Book: Approved Drug Products with Therapeutic Equivalence Evaluations" U.S. Food & Drug Administration, 10 pages.
Exhibit 1057 in IPR 2017-01292 filed Apr. 18, 2017 (Terminated) B. Blackwell, "Treatment Adherence", The British Journal of Psychiatry (1976), 129, 513-531, 20 pages.
Exhibit 1058 in IPR 2017-01292 filed Apr. 18, 2017 (Terminated) C.R. Cunningham, "Maize Starch and Superdisintegrants in a Direct-Compression Formulation", Pharmaceutical Manufacturing Review, Dec. 1999, 2 pages.
Exhibit 1059 in IPR 2017-01292 filed Apr. 18, 2017 (Terminated) Piroxicam, Drugbank, 15 pages.
Exhibit 1060 in IPR 2017-01292 filed Apr. 18, 2017 (Terminated) U.S. Pat. No. 5,532,372, Issued Jul. 2, 1996, 36 pages.
Exhibit 1061 in IPR 2017-01292 filed Apr. 18, 2017 (Terminated) ZELDOX® (Ziprasidone hydrochloride), 23 pages.
Exhibit 1062 in IPR 2017-01292 filed Apr. 18, 2017 (Terminated) ibuprofen, Drugbank, 37 pages.
Exhibit 1063 in IPR 2017-01292 filed Apr. 18, 2017 (Terminated) Azithromycin, Drugbank, 16 pages.
Exhibit 1064 in IPR 2017-01292 filed Apr. 18, 2017 (Terminated) Hydrochlorothiazide, Drugbank, 17 pages.
Exhibit 1065 in IPR 2017-01292 filed Apr. 18, 2017 (Terminated) "Center for Drug Evaluation and Research Application No. 200603 Chemistry Review(s)", 2010, 38 pages.
Exhibit 1066 in IPR 2017-01292 filed Apr. 18, 2017 (Terminated) U.S. Pat. No. 7,727,553, Issued Jun. 1, 2010, 16 pages.
P. Kardas, "Patient compliance with antibiotic treatment for respiratory tract infections", Journal of Antimicrobial Chemotherapy (2002) 49, 897-903.
SD Portsmouth et al., "Better maintained adherence on switching from twice-daily to once-daily therapy for HIV: a 24-week randomized trial of treatment simplification using stavudine prolonged-release capsules", HIV Medicine (2005), 6, 185-190.
G. Moyle et al., "The Assessing Patients' Preferred Treatments (APPT-1) study", International Journal of STD & AIDS, 2003, 14 (Suppl.1), 34-36.
H Hey et al., "Oesophageal transit of six commonly used tablets and capsules", British Medical Journal, vol. 285, 1982, 1717-1719.
A. Raedler et al., "Mesalazine (5-aminosalicylic acid) micropellets show similar efficacy and tolerability to mesalazine tablets in patients with ulcerative colitis—results from a randomized-controlled trial", Alimentary Pharmacology & Therapeutics, 2004, 20, 1353-1363.
H. Takeuchi et al., "Enhancement of the dissolution rate of a poorly water-soluble drug (tolbutamide) by a spray-drying solvent deposition method and disintegrants", Journal of Pharmacy and Pharmacology, 1987, 39, 769-773.
Z.T. Chowhan et al., "Drug-Excipient Interactions Resulting from Powder Mixing 111: Solid State Properties and Their Effect on Drug Dissolution", Journal of Pharmaceutical Sciences, 1986, 75(6), 534-541.
C.R. Cunningham et al., "Formulation of Acetylsalicylic Acid Tablets for Aqueous Enteric Film Coating", Pharmaceutial Technology Drug Delivery, 2001, 38-43.
"Guidance for Industry: Dissolution Testing of Immediate Release Solid Oral Dosage Forms", U.S. Department of Health and Human Services, Food and Drug Administration Center for Drug Evaluation and Research (CDER), published Aug. 1997, 17 pages.
L. L. Augsburger et al., "Tablet Formulation", Encyclopedia of Pharmaceutical Technology, $2^{nd}$ Ed., Marcel Dekker, Inc., 2002, vol. 3, pp. 2701-2712.
RJ Harwood, "Hypromellose", Handbook of Pharmaceutical Excipients, $4^{th}$ Ed., Pharmaceutical Press and the American Pharmaceutical Association, 2003, pp. 297-300.

* cited by examiner

PHARMACEUTICAL COMPOSITION

This is a continuation of prior application Ser. No. 14/512,189, filed Oct. 10, 2014, which is a continuation of prior application Ser. No. 14/183,283, filed Feb. 18, 2014, which is a continuation of application Ser. No. 11/919,678, filed Oct. 31, 2007, which issued on May 20, 2014 as U.S. Pat. No. 8,729,085, which is a National Stage Entry of International Application No. PCT/JP2006/310571, filed May 26, 2006, which claims priority to Japanese Patent Application No. 2005-153508, filed May 26, 2005.

TECHNICAL FIELD

The present invention relates to an oral preparation with a good disintegration which comprises as an active ingredient N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboxyimide hydrochloride (lurasidone). More particularly, the present invention relates to a preparation for oral administration, particularly a tablet, comprising lurasidone as an active ingredient, which has an equivalent dissolution profile of the active ingredient even though contents of the active ingredient therein are varied.

BACKGROUND ART

Patent Document 1 discloses that a compound such as lurasidone can be orally administered and an oral preparation can be prepared by blending an active ingredient with a conventional carrier, excipient, binder, stabilizer and the like, but there is no disclosure of an oral preparation which shows a rapid dissolution and has an equivalent dissolution profile of the active ingredient even though contents of the active ingredient therein are varied in the wide range, particularly an oral preparation with increased contents of the active ingredient which has a similar dissolution profile to that of multiple tablets with a lower content of the active ingredient per tablet.

For the purpose of securing the bioequivalence when pharmaceutical preparations with different contents of the active ingredient were administered so as to be the same dose to each other, a guideline has been issued, i.e., "Guideline for Bioequivalence Studies of Oral Solid Dosage Forms with Different Content" (Notification No. 64 of the Evaluation and Licensing Division, Pharmaceutical and Food Safety Bureau, promulgated on Feb. 14, 2000) by which it has been required that pharmaceutical preparations with different contents should have an equivalent dissolution profile in each test solution such as buffers of pH1.2, 3.0 to 5.0 and 6.8 (which correspond to the pH values of stomach, intestine and oral cavity, respectively), water, and saline.

Patent Document 2 discloses an oral preparation comprising lurasidone as an active ingredient, which shows a rapid dissolution and has an equivalent dissolution profile even though contents of the active ingredient therein are varied, particularly an oral preparation with increased contents of the active ingredient which has an equivalent dissolution profile to that of multiple tablets with a lower content of the active ingredient per tablet and can release a slightly water-soluble active ingredient therefrom at a desired concentration.

Patent Document 2 further discloses an oral preparation, particularly a tablet, which shows a rapid dissolution of the active ingredient even though contents of the active ingredient therein are varied in the range of several mg to several tens of mg (e.g. in the range of 5 mg to 20 mg or in the range of 5 mg to 40 mg), and further has an equivalent dissolution profile in the same componental ratio. An oral preparation has been frequently required to be a preparation with higher contents of the active ingredient in order to get higher clinical effects, or a preparation which has an equivalent dissolution profile to that of multiple tablets and can release the active ingredient therefrom at a desired concentration in wider ranges of contents in order to adjust clinical effects depending on conditions of patients. The art disclosed in Patent Document 2 may provide an oral preparation which has an equivalent dissolution profile in the range of 5 mg to 40 mg of lurasidone per tablet, as shown in FIG. 1. However, as shown in FIG. 2, when the content of the active ingredient per tablet was increased to double, i.e., 80 mg tablet, it could not have an equivalent dissolution profile. Hence, it remains in a state of administering multiple tablets at one time or using a tablet having a big size which is difficult to administer. Therefore, for such a slightly water-soluble active ingredient as lurasidone, it has been difficult to provide an oral preparation having an equivalent dissolution profile even in high content or in wider ranges of contents of the active ingredient.

In Patent Document 2, a water-soluble polymer binder includes starch, but there is no description about a pregelatinized starch therein. The pregelatinized starch is known to remarkably improve a disintegration and a dissolution of a pharmaceutical composition as described, for example, in Patent Document 3, but it is often used, typically, in 10% or less of contents as also described in Non-patent Document 1.

Patent Document 1: JP2800953
Patent Document 2: WO2002/024166
Patent Document 3: JP2000-26292
Non-patent Document 1: Handbook of Pharmaceutical Excipients, 2nd edition, 491, 1994, The Pharmaceutical Press

DISCLOSURE OF INVENTION

Problems to be Resolved by the Invention

The present invention is directed to provide an oral preparation comprising lurasidone as an active ingredient which shows a rapid dissolution and has an equivalent dissolution profile even though contents of the active ingredient therein are varied in the wide range, particularly an oral preparation with increased contents of the active ingredient which has a similar dissolution profile to that of multiple tablets with a lower content of the active ingredient per tablet and can release the active ingredient therefrom at a desired concentration.

The present invention is directed to provide a preparation for oral administration which comprises as an active ingredient N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboxyimide hydrochloride (hereinafter referred to as lurasidone), which has an equivalent dissolution profile of the active ingredient even though contents of the active ingredient therein are varied.

Means of Solving the Problems

The present inventors have intensively studied in order to solve the above problems and found to solve said problems by means of the following methods.

The present invention includes the following embodiments:

(1) An oral preparation which comprises N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboxyimide hydrochloride (lurasidone) of the formula (1):

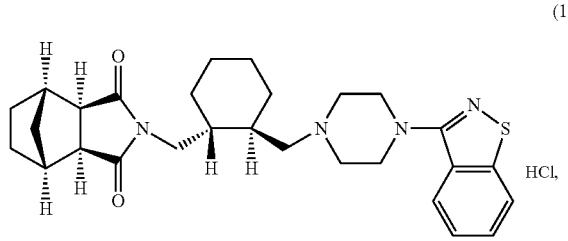

(1)

a pregelatinized starch, a water-soluble excipient and a water-soluble polymer binder.

(2) An oral preparation which is prepared by granulating a powder mixture comprising lurasidone, a pregelatinized starch and a water-soluble excipient by using a solution of a water-soluble polymer binder.

(3) An oral preparation which is prepared by granulating a powder mixture comprising a pregelatinized starch and a water-soluble excipient by a solution or dispersion of lurasidone and a water-soluble polymer binder.

(4) The oral preparation of any one of (1) to (3) wherein the water-soluble excipient is mannitol or lactose.

(5) A method of granulation of a powder mixture which comprises granulating a powder mixture comprising lurasidone, a pregelatinized starch and a water-soluble excipient by using a solution of a water-soluble polymer binder.

(6) A method of granulation of a powder mixture which comprises granulating a powder mixture comprising a pregelatinized starch and a water-soluble excipient by using a solution or dispersion of lurasidone and a water-soluble polymer binder.

(7) The method of granulation of (5) wherein the water-soluble excipient is mannitol or lactose.

(8) The oral preparation of any one of (1) to (4) wherein, the pregelatinized starch is incorporated in an amount of 10 to 50% (wt/wt) based on the weight of the preparation.

(9) The oral preparation of any one of (1) to (4) wherein the pregelatinized starch is incorporated in an amount of 20 to 30% (wt/wt) based on the weight of the preparation.

(10) The oral preparation of any one of (1) to (4) wherein a content of lurasidone in the preparation is 20 to 45% (wt/wt).

(11) The oral preparation of any one of (1) to (4) wherein a content of lurasidone in the preparation is 25 to 40% (wt/wt).

(12) The oral preparation of any one of (1) to (4) wherein a content of lurasidone per tablet is 10 to 160 mg.

(13) The oral preparation of any one of (1) to (4) wherein a content of lurasidone per tablet is 20 to 120 mg.

(14) The oral preparation of any one of (1) to (4) wherein a content of lurasidone per tablet is 40 to 120 mg.

(15) The oral preparation of any one of (1) to (4) wherein the water-soluble excipient is mannitol or lactose and the pregelatinized starch is incorporated in an amount of 10 to 50% (wt/wt) based on the weight of the preparation.

(16) The oral preparation of any one of (1) to (4) wherein the water-soluble excipient is mannitol or lactose and a content of lurasidone in the preparation is 25 to 40% (wt/wt).

(17) The oral preparation of any one of (1) to (4) wherein the pregelatinized starch is incorporated in an amount of 10 to 50% (wt/wt) based on the weight of the preparation and a content of lurasidone in the preparation is 25 to 40% (wt/wt).

(18) The oral preparation of any one of (1) to (4) wherein the water-soluble excipient is mannitol or lactose, the pregelatinized starch is incorporated in an amount of 10 to 50% (wt/wt) based on the weight of the preparation and a content of lurasidone in the preparation is 25 to 40% (wt/wt).

(19) The oral preparation of any one of (1) to (4) wherein the water-soluble excipient is mannitol or lactose, the pregelatinized starch is incorporated in an amount of 20 to 30% (wt/wt) based on the weight of the preparation and a content of lurasidone in the preparation is 25 to 40% (wt/wt).

(20) The oral preparation of any one of (1) to (4) wherein the water-soluble excipient is mannitol or lactose, the pregelatinized starch is incorporated in an amount of 20 to 30% (wt/wt) based on the weight of the preparation and a content of lurasidone per tablet is 40 to 120 mg.

(21) The oral preparation of any one of (1) to (4) wherein a pregelatinization ratio of the pregelatinized starch is 50 to 95%.

(22) The oral preparation of any one of (1) to (4) wherein an average particle size of lurasidone is 0.1 to 8 μm.

(23) The oral preparation of any one of (1) to (4) wherein the pregelatinized starch contains water soluble matter of 30% or less.

(24) The oral preparation of any one of (1) to (4) wherein the water-soluble excipient is mannitol or lactose, the pregelatinized starch is incorporated in an amount of 20 to 30% (wt/wt) based on the weight of the preparation, a content of lurasidone in the preparation is 25 to 40% (wt/wt) and a content of lurasidone per tablet is 20 to 120 mg.

Effects of Invention

It has been confirmed in the art disclosed in Patent Document 2 that a pharmaceutical preparation with low contents of lurasidone up to 40 mg per tablet could provide an oral preparation having an equivalent dissolution profile. However, a pharmaceutical preparation with higher contents of lurasidone could not have an equivalent dissolution profile. Therefore, double amounts or more of the preparation with low contents should have been administered to a patient in need of high doses of lurasidone, which imposed increased burdens on the patient, and hence an improvement thereon has been required. The preparation of the present invention which comprises a pregelatinized starch can provide an oral preparation with higher contents of lurasidone which imposes less of burdens on a patient. Additionally, the present invention can provide an oral preparation with high contents of lurasidone, and a preparation for oral administration which has an equivalent dissolution profile even though contents of lurasidone therein are varied. Moreover, the preparations are excellent for a long-term conservation.

BEST MODE FOR CARRYING OUT THE INVENTION

N-[4-[4-(1,2-benzisothiazol-3-yl)-1-piperazinyl]-(2R,3R)-2,3-tetramethylene-butyl]-(1'R,2'S,3'R,4'S)-2,3-bicyclo

[2,2,1]heptane-dicarboxyimide hydrochloride (lurasidone) refers to a compound of the following formula:

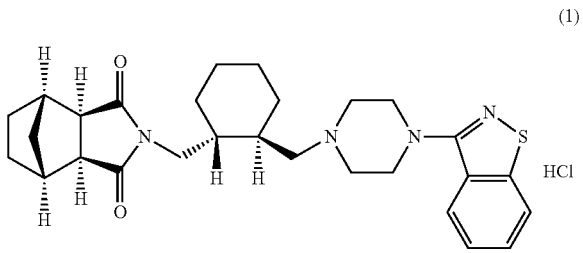 [SMILES: O=C1[C@@H]2[C@H]3CC[C@H](C3)[C@@H]2C(=O)N1C[C@@H]1CCCC[C@H]1CN1CCN(c2nsc3ccccc23)CC1 ; Cl]

(1)

(see, for example, JP2800953). Lurasidone is known to exhibit a psychotropic effect, and it is useful as a therapeutic agent for schizophrenia, etc. Said compound is incorporated into the preparation, for example, in the range of 10 to 50% by weight, preferably in the range of 20 to 45% by weight, particularly in the range of 20 to 45% by weight on the basis of the total weight of a tablet. Additionally, the compound is preferably finely milled, for example, 90% by volume or more of particles have 27 µm or less of particle size, and average particle size in a volume ratio (i.e. 50% by volume particle size) includes, for example, in the range of 0.1 to 8 µm, preferably in the range of 1 to 4 µm. The contents of lurasidone are 10 to 160 mg, preferably 20 to 120 mg, more preferably 40 to 120 mg per tablet.

The "pregelatinized starch" refers to those prepared by pregelatinizing various kinds of starch (e.g. corn starch, potato starch, wheat starch, rice starch, tapioca starch, etc.), and may include pregelatinized starch or partly pregelatinized starch described in Japanese Pharmaceutical Excipients. The pregelatinized starch has a pregelatinization ratio, for example, in the range of 50 to 100%, preferably in the range of 50 to 95%, more preferably in the range of 80 to 95%. Additionally, the pregelatinized starch contains water soluble matter of, for example, 40% or less, more preferably 30% or less. Such a pregelatinized starch is typically used in a powder which average particle size is in the range of 1 to 1000 µm, preferably in the range of 1 to 500 µm, more preferably in the range of 10 to 100 µm. A commercially available pregelatinized starch suitable for the present invention includes, for example, partly pregelatinized starch such as PCS (brand name, manufactured by Asahi Kasei Corporation) or Starch 1500 (brand name, manufactured by Colorcon, Inc.), etc. Among the above pregelatinized starch, partly pregelatinized starch such as PCS (brand name, manufactured by Asahi Kasei Corporation) is preferably used. A pregelatinization ratio of partly pregelatinized starch is preferably in the range of 50 to 95%, more preferably in the range of 80 to 95%. The pregelatinized starch used in the present invention is in the range of 10% to 50%, preferably in the range of 10% to 40%, particularly in the range of 20% to 30% by weight of the preparation.

The "water-soluble excipient" includes, for example, mannitol, lactose, saccharose, sorbitol, D-sorbitol, erythritol, xylitol, etc. More preferable one includes mannitol and lactose. Further preferable one may include mannitol. Also, said water-soluble excipient may be used alone, or two or more thereof may be used together. The water-soluble excipient is incorporated in an amount of, for example, the range of 30 to 80% by weight, preferably the range of 40 to 60% by weight on the basis of the total weight of a tablet. The average particle size of mannitol is, for example, in the range of 10 to 200 µm.

The "water-soluble polymer binder" includes, for example, hydroxypropylcellulose, hydroxypropyl methylcellulose, polyvinylpyrrolidone, polyvinyl alcohol, etc. More preferable one includes hydroxypropylcellulose, hydroxypropyl methylcellulose, polyvinylpyrrolidone or polyvinyl alcohol. Said water-soluble polymer binder may be used alone, or two or more thereof may be used together. The water-soluble polymer binder is incorporated in an amount of, for example, the range of 0.5 to 10% by weight, preferably the range of 1 to 5% by weight on the basis of the total weight of a tablet.

The oral preparation in the form of a pharmaceutical composition of the present invention refers to a pharmaceutical preparation which is formulated into tablet, capsule, granule or fine granule. Said preparation may be formulated by a conventional method into tablet, capsule, granule or fine granule by using water-soluble excipient as well as water-insoluble excipient, binder, disintegrant, lubricant, etc. The following agents may be added thereto.

The "water-insoluble excipient" includes, for example, corn starch, crystalline cellulose, etc. Said water-insoluble excipient may be used alone, or two or more thereof may be used together.

The "disintegrant" includes, for example, corn starch, crystalline cellulose, low substituted hydroxypropylcellulose, carmellose, carmellose calcium, carmellose sodium, croscarmellose sodium, carboxymethyl starch sodium, crospovidone, etc. Said disintegrant may be used alone, or two or more thereof may be used together. The disintegrant is used in an amount of, for example, the range of 0 to 10% by weight, preferably the range of 0.5 to 5% by weight on the basis of the total weight of a tablet.

The "lubricant" includes, for example, magnesium stearate, talc, polyethylene glycol, silica, hydrogenated vegetable oil, etc.

The oral preparation of the present invention may be prepared according to a conventional method depending on a desired dosage form.

(1) Preparation of an Aqueous Solution of Water-Soluble Polymer Binder:

A water-soluble polymer binder is dissolved in purified water. The amount of the water-soluble polymer binder is, for example, in the range of 1 to 20% by weight, preferably in the range of 2 to 8% by weight of purified water.

(2) Preparation of Granule Comprising Lurasidone:

To a fluid bed granulator are charged excipient including lurasidone, mannitol and partly pregelatinized starch, and disintegrant, and thereto is sprayed the water-soluble polymer binder prepared in the above process (1) to be granulated.

The apparatus for granulation includes, for example, one classified into fluid bed granulation, high share granulation, roto fluid bed granulation, etc., but it is not limited thereto.

(3) Drying of Granule:

The above-obtained granule is dried either under reduced pressure or atmospheric pressure. The drying is carried out so that the loss on dry measured by infrared moisture meter is, for example, within 3% by weight, preferably 1 to 2% by weight.

(4) Blending of Lubricant:

To the granule dried in the above (3) is added lubricant to be mixed. For mixing, for example, a blending machine classified into diffusion mixers [Tumble] is used. Specifically, tumble blender, V blenders, double cone, bin tumble, etc. are used, but it is not limited thereto.

(5) Compression:

The above mixture is compressed to give a tablet.

The apparatus for compression includes, for example, one classified into tablet press, etc. The compression hardness is selected, for example, from the range of 30 to 200N.

(6) Film-Coating is Optionally Carried Out:

The above-obtained tablet may be optionally subjected to film-coating, if necessary. The apparatus for coating includes, for example, one classified into a coating pan. Preferable one includes one classified by perforated coating system.

The coating agent includes, for example, a mixture of base material (e.g. hydroxypropyl methylcellulose, hydropropylcellulose, polyvinylpyrrolidone, polyvinyl alcohol, etc.) and plasticizer (e.g. polyethylene glycol, propylene glycol, triacetin, triethyl citrate, glycerin, glycerin fatty acid ester, polyethylene glycol, etc.). If necessary, an additive such as titanium oxide may be also added therein. After film-coating, carnauba wax, etc. may be also added as polishing agent therein.

(7) Drying:

The above-obtained tablet is dried. The drying is carried out either under reduced pressure or atmospheric pressure so that the loss on dry measured by infrared moisture meter is, for example, within 3% by weight, preferably 1 to 2% by weight.

Examples of the present invention are illustrated below. Said examples are intended to exemplify the present invention but not to limit the present invention thereto.

EXAMPLES

Example 1

A. A Film-Coated Tablet Comprising 80 mg of Lurasidone (Example 1)

Granules, uncoated tablets and FC tablets comprising the following components are sequentially prepared. The charging amounts shown in parentheses in the following description are an example for preparing the formulation shown in Example 1.

According to the preparation method, other examples may be also prepared in principle, provided that the charging amounts are needed to be changed depending on formulations.

B. Preparation Method (1) Preparation of Binding Solution (5% Aqueous Hydroxypropyl Methylcellulose Solution):

Hydroxypropyl methylcellulose (32 g) as water-soluble polymer binder was dissolved in purified water (608 g) to give binding solution.

(2) Granulation:

Lurasidone (320 g), mannitol (576 g), partly pregelatinized starch (320 g) and croscarmellose sodium (16 g) were charged to a fluid bed granulator (Multiplex MP-01/manufactured by Powrex Corporation), and the mixture was granulated by spray granulation under the following conditions using the binding solution prepared in the above (1) to give granule powder. To the obtained granule powder was added magnesium stearate to give a granule for compression having a formulation (b) after mixing (40 rpm, 5 minutes). Magnesium stearate was mixed in amounts calculated from a formulation on the basis of yields of granule powder.

Conditions for Granulation
　Temperature for supplying air: 60° C.
　Airflow: 50 to 65 $m^3$/hr
　Spray speed: 13 g/min
　Diameter of spray nozzle: 1.2 mm
　Spray pressure: 0.12 MPa
　Gun position: the middle stand (3) Compression:

The granule for compression prepared in the above (2) was compressed by HT-AP12SS-II (manufactured by Hata Iron Works Co., Ltd.) to give a tablet.
　Pestle size: φ10 mm 14R
　Thickness: 4.20 to 4.30 mm
　Compression pressure: 10 KN (4) Coating:

The uncoated tablet prepared in the above (3) were coated by using High Coater HCT30N (manufactured by Freund Industrial Co., Ltd.) under the following conditions so as to control amounts of the coat to 5 mg, and thereto was added carnauba wax after coating to give a film-coated tablet.

FC Conditions
　Temperature for supplying air: 80° C.
　Airflow: 0.6 $m^3$/min
　Rotation rate of pan: 25 rpm
　Spray pressure: 0.15 MPa
　Liquid flow rate: 5 g/min The preparation obtained in the above method was evaluated a quality thereof according to the following methods, and the present invention has been achieved on the basis of the knowledge obtained therein.

C. Quality Evaluation (1) Dissolution Test

A manufactured preparation was subjected to the dissolution test according to the Japanese Pharmacopoeia, Dissolution test, Method 2.

Measuring conditions are shown below.
　Test solution: Diluted McIlvaine buffer, pH4.0
　Rotation rate of paddle: 50 rpm
　Test fluid: 900 ml (2) Similarity of Dissolution Profiles A similarity factor f2 shown in Scale-Up and Past-Approval Changes for Intermediate Release Products (SUPAC-IR) was used as an indicative for evaluating a similarity of dissolution profiles. The f2 value is calculated by the following equation. It was determined that each manufactured preparation had a similar dissolution profile in case that the f2 value calculated from dissolution ratio of each preparation by SUPAC-IR was in the range of 50≤f2≤100. Dissolution ratios at three time points such as 15 min, 30 min and 45 min after starting the test were used for a calculation of the f2 value.

$$f2 = 50 \cdot \mathrm{LOG}\left[\frac{100}{\sqrt{1+\frac{\sum_{i=1}^{n}(Ti-Ri)^2}{n}}}\right]$$

Ti and Ri are the percent dissolved at each point.
n is the number of points to be compared.

(3) Size Distribution

A size distribution of lurasidone was measured according to a dry-spray method by Laser Diffraction Particle Size Analyzer (SLAD-3000/Shimadzu Corporation). Measuring conditions are shown below.

| | | | | |
|---|---|---|---|---|
| Amounts of sample: 2 g | | | | |
| Air pressure: 0.4 MPa or more | | | | |
| Turntable rotation speed: 2 | | | | |
| Parameter setting | | | | |
| Environmental setting | | | | |
| Monitoring average: | 16 | Measuring optimum range | | |
| Dark measuring average: | 2 | (Max): | | 1500 |
| Light intensity display Max: | 2000 | (Min): | | 700 |
| Previous blank: | reading | (CH-1) baud rate (bps): | | 9600 |
| Printer: | monochrome | Blank measurable Max: | | 300 |
| | | Blank measurable variation range: | | 20 |
| Refractive parameter | | | | |
| Standard refraction: | 1.70-0.20i | | | |
| Measuring conditions setting | | | | |
| Measuring average: | 1 | Dry permissible Min: | | 300 |
| Measuring interval (sec): | 1 | Max: | | 2500 |
| Average: | 64 | Granule range for evaluation (Min): | | 0.1 |
| Measured absorbance range (Max): | 0.1 | Granule range for evaluation (Max): | | 2000 |
| (Min): | 0.05 | | | |
| Trigger mode: | OFF | Start position of sensor usage: | | 1 |
| Dry threshold: | 300 | | | |

<Test 1>

In Examples 1, 2 and 3, tablets comprising specific pharmaceutical compositions comprising water-soluble excipient comprising 20 mg, 40 mg and 80 mg, respectively, of lurasidone per tablet, partly pregelatinized starch and water-soluble polymer binder were manufactured. In Comparative experiments 1 and 2, tablets comprising 40 mg and 80 mg, respectively, of lurasidone per tablet were manufactured on the basis of the formulation disclosed in Patent Document 2.

The manufactured preparations were subjected to the dissolution tests under conditions shown in (d) and (e), and similarities of dissolution profiles were evaluated. Additionally, preproductions in Comparative experiments 1 and 2 were shown in Test 8.

Results were shown in Tables 4 and 5. Temporal dissolution ratios in (d) were shown in FIGS. 2 and 3.

(a) Formulations of Granule Powders

TABLE 1

| | Example No. | | | Compar. Ex. No. | |
|---|---|---|---|---|---|
| | | | | | Unit: mg |
| Component | 1 | 2 | 3 | 1 | 2 |
| Lurasidone | 80 | 40 | 20 | 40 | 80 |
| Mannitol | 144 | 72 | 36 | 188 | 148 |
| Partly pregelatinized starch | 80 | 40 | 20 | — | — |
| Croscarmellose sodium | 4 | 2 | 1 | 16 | 16 |
| Hydroxypropyl methylcellulose | 8 | 4 | 2 | 10 | 10 |

(b) Formulations of Granules for Compression/Uncoated Tablets

TABLE 2

| | Example No. | | | Compar. Ex. No. | |
|---|---|---|---|---|---|
| | | | | | Unit: mg |
| Component | 1 | 1 | 1 | 1 | 2 |
| Granules in the above (a) | 316 | 158 | 79 | 254 | 254 |
| Lactose | — | — | — | 62 | 62 |
| Magnesium stearate | 4 | 2 | 1 | 4 | 4 |

(c) Formulations of FC Tablets

TABLE 3

| | Example No. | | | Compar. Ex. No. | |
|---|---|---|---|---|---|
| | | | | | Unit: mg |
| Component | 1 | 2 | 3 | 1 | 2 |
| Uncoated tablets in the above (b) | 320 | 160 | 80 | 320 | 320 |
| Hydroxypropyl methylcellulose | 3.25 | 1.95 | 1.3 | 2.6 | 2.6 |
| Titanium oxide | 1 | 0.6 | 0.4 | 0.8 | 0.8 |
| Polyethylene glycol 6000 | 0.75 | 0.45 | 0.3 | 0.6 | 0.6 |
| Carnauba wax | 0.01 | 0.006 | 0.004 | 0.01 | 0.01 |

(d) Dissolution Test in the System Comprising 80 mg of Lurasidone in Each Vessel Each film-coated tablet comprising 80 mg, 40 mg or 20 mg of lurasidone in the system comprising 80 mg of lurasidone in each vessel was subjected to the dissolution test, and a similarity of each dissolution profile was evaluated by f2 value.

As evidenced by Table 4, f2 values in Examples 2 and 3 showed similarities to Example 1, but f2 value in Comparative experiment 2 did not show a similarity to Comparative experiment 1. In other words, as evidenced by Table 4 and FIG. 3, in Examples 1 to 3, f2 values which represented similarities of dissolution profiles were in the range of $50 \leq f2 \leq 100$, and preparations which showed similarities of dissolution profiles without depending on contents in tablets (unit strength) even in preparations with different contents were obtained. On the other hand, as evidenced by Table 4 and FIG. 2, dissolution of the formulation disclosed in Patent Document 2 in Comparative experiment 2 was apparently slower than that of two tablets of preparations in Comparative experiment 1, and a similarity of dissolution profile was not shown as detailed in Test 8.

TABLE 4

| | Example No. | | | Compar. Ex. No. | |
|---|---|---|---|---|---|
| Similarity factor | 1 | 2 | 3 | 1 | 2 |
| f2 | — | 88 | 97 | — | 37 |

(e) Dissolution Test in the System Comprising 40 mg of Lurasidone in Each Vessel Each film-coated tablet comprising 40 mg or 20 mg of lurasidone in the system comprising 40 mg of lurasidone in each vessel was subjected to the dissolution test, and a similarity of each dissolution profile was evaluated by using f2 values in the similar manner.

As evidenced by Table 5, f2 values in Example 3 and Comparative experiment 1 showed similarities to Example 2. In other words, f2 values were in the range of $50 \leq f2 \leq 100$ even in the system comprising 40 mg of lurasidone in each vessel, and similarities of dissolution profiles were shown without depending on contents in tablets (unit strength).

TABLE 5

| Similarity factor | Example No. | | Compar. Ex. No. |
|---|---|---|---|
| | 2 | 3 | 1 |
| f2 | — | 88 | 97 |

<Test 2>

Preparations comprising a pharmaceutical composition comprising water-soluble excipient and water-soluble polymer binder and partly pregelatinized starch were prepared in Examples 1 and 4. Preparations comprising a pharmaceutical composition comprising water-soluble excipient and water-soluble polymer binder and corn starch which was non-pregelatinized starch were prepared in Comparative experiments 3, 4 and 5. Each preparation was subjected to the dissolution test, and a similarity of each dissolution profile was evaluated by f2 value. Results were shown in Table 9.

(a) Formulations of Granule Powders

TABLE 6

Unit: mg

| Component | Example No. | | Compar. Ex. No. | | |
|---|---|---|---|---|---|
| | 1 | 4 | 3 | 4 | 5 |
| Lurasidone | 80 | 80 | 80 | 80 | 80 |
| Mannitol | 144 | 176 | 108 | 108 | — |
| Lactose | — | — | — | — | 108 |
| Partly pregelatinized starch | 80 | 40 | — | — | — |
| Corn starch | — | — | 40 | 40 | 40 |
| Croscarmellose sodium | 4 | 8 | 16 | 16 | 16 |
| Hydroxypropyl methylcellulose | 8 | 12 | 10 | 10 | 10 |

(b) Formulations of Granules for Compression/Uncoated Tablets

TABLE 7

Unit: mg

| Component | Example No. | | Comparative Example No. | | |
|---|---|---|---|---|---|
| | 1 | 4 | 3 | 4 | 5 |
| Granules in the above (a) | 316 | 316 | 254 | 254 | 254 |
| Mannitol | — | — | 62 | — | — |
| Magnesium stearate | 4 | 4 | 4 | 4 | 4 |

(c) Formulations of FC Tablets

TABLE 8

Unit: mg

| Component | Example No. | | Comparative Example No. | | |
|---|---|---|---|---|---|
| | 1 | 4 | 3 | 4 | 5 |
| Uncoated tablets in the above (b) | 320 | 320 | 320 | 258 | 258 |
| Hydroxypropyl methylcellulose | 3.25 | — | 2.6 | 2.6 | 2.6 |
| Titanium oxide | 1 | — | 0.8 | 0.8 | 0.8 |
| Polyethylene glycol 6000 | 0.75 | — | 0.6 | 0.6 | 0.6 |

(d) Dissolution Test

As evidenced by Table 9, Example 4 showed a similarity to Example 1, but f2 values in Comparative experiments 3, 4 and 5 did not show similarities to Example 1. In other words, preparations containing corn starch in Comparative experiments 3, 4 and 5 showed different dissolution profiles and slow dissolutions compared to preparations containing partly pregelatinized starch in Examples 1 and 4.

TABLE 9

| Similarity factor | Example No. | | Comparative Ex. No. | | |
|---|---|---|---|---|---|
| | 1 | 4 | 3 | 4 | 5 |
| f2 | — | 67 | 44 | 29 | 26 |

<Test 3>

Effects of blending quantities of partly pregelatinized starch in Examples 4, 5, 6 and 7 on dissolutions were evaluated. Results were shown in Table 13.

(a) Formulations of Granule Powders

TABLE 10

Unit: mg

| Component | Example No. | | | | |
|---|---|---|---|---|---|
| | 1 | 4 | 5 | 6 | 7 |
| Lurasidone | 80 | 80 | 80 | 80 | 80 |
| Mannitol | 144 | 176 | 116 | 136 | 156 |
| Partly pregelatinized starch | 80 | 40 | 100 | 80 | 60 |
| Croscarmellose sodium | 4 | 8 | 8 | 8 | 8 |
| Hydroxypropyl methylcellulose | 8 | 12 | 12 | 12 | 12 |

(b) Formulations of Granules for Compression/Uncoated Tablets

TABLE 11

Unit: mg

| Component | Example No. | | | | |
|---|---|---|---|---|---|
| | 1 | 4 | 5 | 6 | 7 |
| Granules in the above (a) | 316 | 316 | 316 | 316 | 316 |
| Magnesium stearate | 4 | 4 | 4 | 4 | 4 |

(c) Formulations of FC Tablets

TABLE 12

Unit: mg

| Component | Example No. | | | | |
|---|---|---|---|---|---|
| | 1 | 4 | 5 | 6 | 7 |
| Uncoated tablets in the above (b) | 320 | 320 | 320 | 320 | 320 |
| Hydroxypropyl methylcellulose | 3.25 | — | — | — | — |
| Titanium oxide | 1 | — | — | — | — |
| Polyethylene glycol 6000 | 0.75 | — | — | — | — |
| Carnauba wax | 0.01 | — | — | — | — |

(d) Dissolution Test

As evidenced by Table 13, f2 values in Examples 4, 5, 6 and 7 showed similarities to Example 1. In other words, a preparation comprising a pharmaceutical composition comprising 10% wt/wt or more of partly pregelatinized starch in preparation components showed a rapid dissolution and a similar dissolution profile.

TABLE 13

| Similarity factor | Example No. | | | | |
|---|---|---|---|---|---|
| | 1 | 4 | 5 | 6 | 7 |
| f2 | — | 67 | 60 | 62 | 81 |

<Test 4>

In Comparative experiment 6, a tablet was tried to be prepared with containing water-soluble excipient and partly pregelatinized starch but without water-soluble polymer binder. However, in a compression step, components could not be compressed due to capping and sticking, and no similar dissolution profile or even tablet was obtained. In Examples 8, 9, 10 and 11, preparations comprising pharmaceutical compositions with different blending quantities of water-soluble excipient and partly pregelatinized starch and water-soluble polymer binder were prepared. Results were shown in Table 17.

(a) Formulations of Granule Powders

TABLE 14

| | Example No. | | | | | Unit: mg Compar. |
|---|---|---|---|---|---|---|
| Component | 1 | 8 | 9 | 10 | 11 | Ex. No. 6 |
| Lurasidone | 80 | 80 | 80 | 80 | 80 | 80 |
| Mannitol | 144 | 136 | 138 | 140 | 142 | 148 |
| Partly pregelatinized starch | 80 | 80 | 80 | 80 | 80 | 80 |
| Croscarmellose sodium | 4 | 8 | 8 | 8 | 8 | 8 |
| Hydroxypropyl methylcellulose | 8 | 12 | 10 | 8 | 6 | — |

(b) Formulations of Granules for Compression/Uncoated Tablets

TABLE 15

| | Example No. | | | | | Unit: mg Compar. |
|---|---|---|---|---|---|---|
| Component | 1 | 8 | 9 | 10 | 11 | Ex. No. 6 |
| Granules in the above (a) | 316 | 316 | 316 | 316 | 316 | 316 |
| Magnesium stearate | 4 | 4 | 4 | 4 | 4 | 4 |

(c) Formulations of FC Tablets

TABLE 16

| | Example No. | | | | | Unit: mg Compar. |
|---|---|---|---|---|---|---|
| Component | 1 | 8 | 9 | 10 | 11 | Ex. No. 6 |
| Uncoated tablets in the above (b) | 320 | 320 | 320 | 320 | 320 | 320 |
| Hydroxypropyl methylcellulose | 3.25 | — | — | — | — | — |
| Titanium oxide | 1 | — | — | — | — | — |
| Polyethylene glycol 6000 | 0.75 | — | — | — | — | — |
| Carnauba wax | 0.01 | — | — | — | — | — |

(d) Dissolution Test

As evidenced by Table 17, f2 values in Examples 8, 9, 10 and 11 showed similarities to Example 1. In other words, preparations comprising pharmaceutical compositions comprising water-soluble polymer binder in the range of 1.8% wt/wt to 3.8% wt/wt showed rapid dissolutions and similar dissolution profiles.

TABLE 17

| Similarity factor | Example No. | | | | |
|---|---|---|---|---|---|
| | 1 | 8 | 9 | 10 | 11 |
| f2 | — | 77 | 81 | 73 | 73 |

<Test 5>

In Example 12, a preparation comprising a pharmaceutical composition comprising water-soluble polymer binder and partly pregelatinized starch was prepared by using lactose as water-soluble excipient. Results were shown in Table 21.

(a) Formulations of Granule Powders

TABLE 18

| | Example No. | | | Unit: mg |
|---|---|---|---|---|
| Component | 1 | 6 | 12 | |
| Lurasidone | 80 | 80 | 80 | |
| Mannitol | 144 | 136 | — | |
| Lactose | — | — | 136 | |
| Partly pregelatinized starch | 80 | 80 | 80 | |
| Croscarmellose sodium | 4 | 8 | 8 | |
| Hydroxypropyl methylcellulose | 8 | 12 | 12 | |

(b) Formulations of Granules for Compression/Uncoated Tablets

TABLE 19

| | Example No. | | | Unit: mg |
|---|---|---|---|---|
| Component | 1 | 6 | 12 | |
| Granules in the above (a) | 316 | 316 | 316 | |
| Magnesium stearate | 4 | 4 | 4 | |

(c) Formulations of FC Tablets

TABLE 20

| | Example No. | | | Unit: mg |
|---|---|---|---|---|
| Component | 1 | 6 | 12 | |
| Uncoated tablets in the above (b) | 320 | 320 | 320 | |
| Hydroxypropyl methylcellulose | 3.25 | — | — | |
| Titanium oxide | 1 | — | — | |
| Polyethylene glycol 6000 | 0.75 | — | — | |
| Carnauba wax | 0.01 | — | — | |

(d) Dissolution Test

As evidenced by Table 21, f2 values in Examples 6 and 12 showed similarities to Example 1. In other words, preparations containing mannitol and lactose as water-soluble excipient showed rapid dissolutions and similar dissolution profiles.

TABLE 21

| Similarity factor | Example No. | | |
|---|---|---|---|
| | 1 | 6 | 12 |
| f2 | — | 62 | 66 |

<Test 6>

In Examples 4, 13, 14 and 15, preparations comprising a specific pharmaceutical composition comprising water-soluble excipient and water-soluble polymer binder and partly pregelatinized starch were prepared by using lurasidone bulk powders with different size distribution. Results were shown in Table 25.

(a) Size Distribution of Lurasidone Bulk Powders

D50% (50% particle size) represents a particle size at a point where an integrated distribution calculated on the basis of volume is 50%, and D90% (90% particle size) represents a particle size at a point where an integrated distribution calculated on the basis of volume is 90% (under sieving).

TABLE 22

Unit: mg

| Size distribution | | Example No. | | | |
|---|---|---|---|---|---|
| | | 4 | 13 | 14 | 15 |
| Particle size | D10 % | 0.5 | 0.9 | 1.0 | 1.5 |
| | D50 % | 1.6 | 5.9 | 7.6 | 13.9 |
| | D90 % | 4.7 | 17.5 | 26.9 | 58.3 |

(b) Formulations of Granules for Compression/Uncoated Tablets

TABLE 23

Unit: mg

| Component | Example No. | | | |
|---|---|---|---|---|
| | 4 | 13 | 14 | 15 |
| Lurasidone | 80 | 80 | 80 | 80 |
| Mannitol | 176 | 144 | 144 | 144 |
| Partly pregelatinized starch | 40 | 80 | 80 | 80 |
| Croscarmellose sodium | 8 | 4 | 4 | 4 |
| Hydroxypropyl methylcellulose | 12 | 8 | 8 | 8 |
| Magnesium stearate | 4 | 4 | 4 | 4 |

(c) Formulations of FC Tablets

TABLE 24

Unit: mg

| Component | Example No. | | | |
|---|---|---|---|---|
| | 4 | 13 | 14 | 15 |
| Uncoated tablets in the above (b) | 320 | 320 | 320 | 320 |
| Hydroxypropyl methylcellulose | — | 3.25 | 3.25 | 3.25 |
| Titanium oxide | — | 1 | 1 | 1 |
| Polyethylene glycol 6000 | — | 0.75 | 0.75 | 0.75 |
| Carnauba wax | — | 0.01 | 0.01 | 0.01 |

(d) Dissolution Test

As evidenced by Table 25, f2 values in Examples 13, 14 and 15 showed similarities to Example 4. In other words, it was found that preparations prepared by using lurasidone bulk powders wherein 50% particle size is in the range of 1 to 8 μm and 90% particle size is 27 μm or less in size distribution showed similar dissolution profiles.

TABLE 25

| Similarity factor | Example No. | | | |
|---|---|---|---|---|
| | 4 | 13 | 14 | 15 |
| f2 | — | 56 | 56 | 46 |

<Test 7>

Preparations wherein contents of lurasidone per tablet were 10 mg and 40 mg were manufactured by using the art disclosed in Patent Document 2, and were subjected to examination if they could provide preparations for oral administration with equivalent dissolution profiles in the range of 10 mg to 40 mg of lurasidone contents per tablet as disclosed in the document 2. Results were shown in FIG. 1.

As evidenced by FIG. 1, dissolution profiles of preparations with different contents of lurasidone obtained by the art disclosed in Patent Document 2 were shown by f2 values, and tablets with 10 mg and 40 mg of lurasidone per tablet could provide preparations for oral administration with equivalent dissolution profiles as described in Patent Document 2.

(a) Formulations of Granules

TABLE 26

Unit: mg

| Component | 10 mg tablet | 40 mg tablet |
|---|---|---|
| Lurasidone | 10 | 40 |
| Mannitol | 47 | 188 |
| Croscarmellose sodium | 4 | 16 |
| Hydroxypropyl methylcellulose | 2.5 | 10 |

(b) Formulations of Uncoated Tablets

TABLE 27

Unit: mg

| Component | 10 mg tablet | 40 mg tablet |
|---|---|---|
| Granules in (a) | 63.5 | 254 |
| Lactose | 15.5 | 62 |
| Magnesium stearate | 1 | 4 |

(c) Formulations of FC Tablets

TABLE 28

Unit: mg

| Component | 10 mg tablet | 40 mg tablet |
|---|---|---|
| Uncoated tablets in the above (b) | 80 | 320 |
| Hydroxypropyl methylcellulose | 1.3 | 2.6 |
| Titanium oxide | 0.4 | 0.8 |
| Polyethylene glycol 6000 | 0.3 | 0.6 |
| Carnauba wax | 0.006 | 0.01 |

<Test 8>

It could be confirmed that a preparation with up to 40 mg of lurasidone per tablet could provide an oral preparation with equivalent dissolution profile in the art disclosed in Patent Document 2. A preparation wherein contents of lurasidone were 80 mg per tablet without containing partly pregelatinized starch was manufactured herein according to the art disclosed in Patent Document 2. The preparation was prepared by doubling a content ratio of the active ingredient so that a tablet weight thereof was the same as 40 mg tablet, in order to avoid an increased strain on a patient associated with growth of tablets in size. Results of Comparative experiments 1 and 2 were shown in Table 4 and FIG. 2.

As evidenced by Table 4 and FIG. 2, 80 mg tablet with double content ratios of lurasidone without containing pregelatinized starch could not show equivalent dissolution to two tablets of 40 mg tablet as shown by f2 values in the art disclosed in Patent Document 2.

(a) Formulations of Granules

TABLE 29

| Component | 40 mg tablet | 80 mg tablet |
|---|---|---|
| | | Unit: mg |
| Lurasidone | 40 | 80 |
| Mannitol | 188 | 148 |
| Croscarmellose sodium | 16 | 16 |
| Hydroxypropyl methylcellulose | 10 | 10 |

(b) Formulations of Uncoated Tablets

TABLE 30

| Component | 40 mg tablet | 80 mg tablet |
|---|---|---|
| | | Unit: mg |
| Granules in (a) | 254 | 254 |
| Lactose | 62 | 62 |
| Magnesium stearate | 4 | 4 |

(c) Formulations of FC Tablets

TABLE 31

| | 40 mg tablet | 80 mg tablet |
|---|---|---|
| | | Unit: mg |
| Uncoated tablets in the above (b) | 320 | 320 |
| Hydroxypropyl methylcellulose | 2.6 | 2.6 |
| Titanium oxide | 0.8 | 0.8 |
| Polyethylene glycol 6000 | 0.6 | 0.6 |
| Carnauba wax | 0.01 | 0.01 |

<Test 9>

Dissolutions of three kinds of preparations with different contents manufactured in Examples 1 to 3 of Test 1 were evaluated. Results were shown in FIG. 3.

As evidenced by FIG. 3, it was confirmed that preparations of the present invention which contained in the range of 20 mg to 80 mg of lurasidone per tablet showed equivalent dissolutions without depending on tablet contents (unit strength).

(a) Formulations of Granule Powders

TABLE 32

| Component | 80 mg tablet | 40 mg tablet | 20 mg tablet |
|---|---|---|---|
| | | | Unit: mg |
| Lurasidone | 80 | 40 | 20 |
| Mannitol | 144 | 72 | 36 |
| Partly pregelatinized starch | 80 | 40 | 20 |
| Croscarmellose sodium | 4 | 2 | 1 |
| Hydroxypropyl methylcellulose | 8 | 4 | 2 |

(b) Formulations of Granules for Compression/Uncoated Tablets

TABLE 33

| Component | 80 mg tablet | 40 mg tablet | 20 mg tablet |
|---|---|---|---|
| | | | Unit: mg |
| Granules in the above (a) | 316 | 158 | 79 |
| Lactose | — | — | — |
| Magnesium stearate | 4 | 2 | 1 |

(c) Formulations of FC Tablets

TABLE 34

| Component | 80 mg tablet | 40 mg tablet | 20 mg tablet |
|---|---|---|---|
| | | | Unit: mg |
| Uncoated tablets in the above (b) | 320 | 160 | 80 |
| Hydroxypropyl methylcellulose | 3.25 | 1.95 | 1.3 |
| Titanium oxide | 1 | 0.6 | 0.4 |
| Polyethylene glycol 6000 | 0.75 | 0.45 | 0.3 |
| Carnauba wax | 0.01 | 0.006 | 0.004 |

<Test 10>

Lurasidone 120 mg tablet preparations wherein each tablet weight was equal were prepared according to the art disclosed in the present invention as well as Patent Document 2, and dissolution profile of each preparation was evaluated.

(a) Experimental Method

Lurasidone 120 mg tablet preparations were manufactured according to the preparation method of the present invention as well as Preparation method 2 in Patent Document 2 (described hereinafter) (Table 35). These manufactured preparations were subjected to the dissolution test on partly changed conditions described in C. Quality evaluation (1) dissolution test in the Example in the present specification.

The dissolution test was carried out by changing pH4.0 to pH3.8 in pH of the test solution diluted McIlvaine buffer.

(b) Preparation Method of the Present Invention

To a fluid bed granulator (Flow Coater FLF-30/manufactured by Freund Industrial Co., Ltd.) were charged lurasidone (8000 g), D-mannitol (14200 g), partly pregelatinized starch (8000 g) and croscarmellose sodium (400 g), and thereto was sprayed 5% hydroxypropyl methylcellulose solution previously prepared to be granulated on conditions that intake temperature was 80° C., intake airflow was 7 m$^3$/m$^{in}$, spray liquid flow rate was 200 mL/min and atomizing airflow was 200 L/min. The obtained granule was dried in the granulator on conditions that drying temperature was 80° C. and drying time was 10 minutes, and it was confirmed by a halogen moisture analyzer that the loss on dry was within 2%. The obtained granule was sized by using a sizing machine (Fiore F-0 type). Then, the sized granule (18000 g) and magnesium stearate (228 g) were blended together by using a blending machine (container size 110 L) on conditions that rotation rate was 20 rpm and blending time was 5 minutes. Finally, the obtained mixture was compressed at a compressing pressure of 12.5 kN by using a compression apparatus (HT-AP12SS-II/manufactured by Hata Iron Works Co., Ltd.) to prepare a lurasidone 120 mg uncoated tablet.

(c) Preparation Method 2 in Patent Document 2

To a fluid bed granulator (Multiplex MP-01/manufactured by Powrex Corporation) were charged lurasidone (160 g), D-mannitol (296 g) and croscarmellose sodium (32 g), and thereto was sprayed 5% hydroxypropyl methylcellulose solution previously prepared to be granulated on conditions that temperature for supplying air was 60° C. and granulating time was 45 minutes. The obtained granule was dried in the granulator on conditions that drying temperature was 80° C. and drying time was 5 minutes, and it was confirmed by a halogen moisture analyzer that the loss on dry was within 1%. Then, the obtained granule (254 g) and lactose (62 g) were blended together by using a blending machine (manufactured by Tsutsui Rikagaku Kikai Co., Ltd.) on conditions that rotation rate was 40 rpm and blending time was 30 minutes. After that, the resulting mixture (316 g) and magnesium stearate (4 g) were blended together by using a blending machine (manufactured by Tsutsui Rikagaku Kikai Co., Ltd.) on conditions that rotation rate was 40 rpm and blending time was 5 minutes. Finally, the obtained mixture was compressed at a compressing pressure of 12.5 kN by using a compression apparatus (HT-AP12SS-II/manufactured by Hata Iron Works Co., Ltd.) to prepare a lurasidone 120 mg uncoated tablet.

(d) Results

Components of the manufactured preparations and results of the dissolution tests were shown below.

TABLE 35

Components of tablets

| | Formulations | |
|---|---|---|
| | 034-15-120-1000 (Disclosure of the present application) | RP-03323-120-1000 (Disclosure of Patent Document 2) |
| Lurasidone | 120 | 120 |
| Mannitol | 213 | 222 |
| Partly pregelatinized starch | 120 | — |
| Croscarmellose sodium | 6 | 24 |
| Tablettose 70 | — | 93 |
| Hydroxypropyl methylcellulose | 15 | 15 |
| Magnesium stearate | 6 | 6 |
| Total | 480 | 480 |

Dissolution profile

| Time (min) | Dissolution rate (%) | |
|---|---|---|
| 10 | 83 | 54 |
| 15 | 91 | 66 |
| 30 | 95 | 80 |
| 45 | 96 | 84 |
| f2 value | — | 37 |

As a result, it was confirmed that lurasidone 120 mg tablet manufactured according to the disclosure of the present application showed more rapid dissolution compared to lurasidone 120 mg tablet manufactured according to the disclosure of Patent Document 2.

<Test 11>

Applied content ranges of drug substance of the present invention were evaluated on the basis of dissolution profiles of preparations.

(a) Experimental Method

Lurasidone 80 mg tablets were manufactured according to the preparation method of the present invention (Table 36). These manufactured preparations were subjected to the dissolution test on conditions described in C. Quality evaluation (1) dissolution test in the Example in the present specification.

(b) Preparation Method

To a fluid bed granulator (Multiplex MP-01/manufactured by Powrex Corporation) were charged lurasidone, D-mannitol, partly pregelatinized starch and croscarmellose sodium, and thereto was sprayed 5% hydroxypropyl methylcellulose solution previously prepared to be granulated on conditions that temperature for supplying air was 60° C. and granulating time was 45 minutes or 60 minutes. The obtained granule was dried in the granulator on conditions that drying temperature was 80° C. and drying time was 5 minutes, and it was confirmed by a halogen moisture analyzer that the loss on dry was within 2%. Then, the obtained granule and magnesium stearate were blended together by using a blending machine (manufactured by Tsutsui Rikagaku Kikai Co., Ltd.) on conditions that rotation rate was 40 rpm and blending time was 5 minutes. Finally, the obtained mixture was compressed at a compressing pressure of 10 kN by using a compression apparatus (HT-AP12SS-II/manufactured by Hata Iron Works Co., Ltd.) to prepare a lurasidone 80 mg uncoated tablet.

(c) Results

Components of manufactured preparations and results of dissolution tests were shown below.

TABLE 36

| | Formulations | | | |
|---|---|---|---|---|
| | 034-15-80-1000 | RP-03320 | RP-03321 | RP-03322 |
| Lurasidone | 80 | 80 | 80 | 80 |
| Mannitol | 142 | 104 | 67 | 30 |
| Partly pregelatinized starch | 80 | 80 | 80 | 80 |
| Croscarmellose sodium | 4 | 4 | 4 | 4 |
| Hydroxypropyl methylcellulose | 10 | 8 | 6 | 4 |
| Magnesium stearate | 4 | 4 | 3 | 2 |
| Total | 320 | 280 | 240 | 200 |

Dissolution profile

| Time (min) | Dissolution ratio (%) | | | |
|---|---|---|---|---|
| 10 | 85 | 73 | 71 | 68 |
| 15 | 89 | 80 | 80 | 81 |
| 30 | 93 | 88 | 88 | 89 |
| 45 | 94 | 90 | 91 | 91 |
| f2 value | — | 60 | 60 | 63 |

As a result, it could be confirmed that similar dissolution profiles were shown by components of preparations wherein lurasidone was contained in the range of 25 to 40%.

<Test 12>

Dissolution profiles of preparations were evaluated for the water-soluble polymer binders of the present invention.

(a) Experimental Method

Lurasidone 80 mg tablet was manufactured according to the preparation method of the present invention (Table 37). These manufactured preparations were subjected to the dissolution test on conditions described in C. Quality evaluation (1) dissolution test in Example in the present specification.

(b) Preparation Method

To a fluid bed granulator (Multiplex MP-01/manufactured by Powrex Corporation) were charged lurasidone (160 g), D-mannitol (284 g), partly pregelatinized starch (160 g) and croscarmellose sodium (8 g), and thereto was sprayed 5% water-soluble polymer binder solution previously prepared to be granulated on conditions that temperature for supplying air was 60° C. and granulating time was 45 minutes. The obtained granule was dried in the granulator on conditions that drying temperature was 80° C. and drying time was 5 minutes, and it was confirmed by a halogen moisture analyzer that the loss on dry was within 2%. Then, the obtained granule and magnesium stearate were blended together by using a blending machine (manufactured by Tsutsui Rikagaku Kikai Co., Ltd.) on conditions that rotation rate was 40 rpm and blending time was 5 minutes. Finally, the obtained mixture was compressed at a compressing pressure of 10 kN by using a compression apparatus (HT-AP12SS-II/manufactured by Hata Iron Works Co., Ltd.) to prepare a lurasidone 80 mg uncoated tablet.

(c) Results

Components of manufactured preparations and results of dissolution tests were shown below.

TABLE 37

| | Formulations | | | |
|---|---|---|---|---|
| | 034-15-80-1000 | RP-03326 | RP-03327 | RP-03328 |
| Lurasidone | 80 | 80 | 80 | 80 |
| Mannitol | 142 | 142 | 142 | 142 |
| Partly pregelatinized starch | 80 | 80 | 80 | 80 |
| Croscarmellose sodium | 4 | 4 | 4 | 4 |
| Hydroxyproplyl methylcellulose | 10 | — | — | — |
| Polyvinyl-alcohol | — | 10 | — | — |
| Polyvinyl-pyrrolidone | — | — | 10 | — |
| Hydroxypropyl-cellulose | — | — | — | 10 |
| Magnesium stearate | 4 | 4 | 4 | 4 |
| Total | 320 | 320 | 320 | 320 |

| Dissolution profile | | | | |
|---|---|---|---|---|
| Time (min) | Dissolution ratio (%) | | | |
| 10 | 83 | 59 | 78 | 80 |
| 15 | 91 | 76 | 82 | 87 |
| 30 | 95 | 94 | 88 | 91 |
| 45 | 96 | 96 | 90 | 92 |
| f2 value | — | 53 | 56 | 69 |

As a result, it was confirmed that preparations using as water-soluble polymer binder polyvinyl alcohol, polyvinylpyrrolidone or hydroxypropylcellulose met the standard of "C. Quality evaluation (2) Similarity of dissolution profiles" in the present specification (similar dissolution profiles).

<Test 13>

Dissolution profiles of lurasidone 20, 40, 80 and 120 mg FC tablets prepared according to the art disclosed in the present invention were evaluated.

(a) Experimental Method

Lurasidone 20, 40, 80 and 120 mg FC tablets were manufactured according to the preparation method of the present invention (Table 38).

(b) Preparation Method

To a fluid bed granulator (Flow Coater FLF-30/manufactured by Freund Industrial Co., Ltd.) were charged lurasidone (8000 g), D-mannitol (14200 g), partly pregelatinized starch (8000 g) and croscarmellose sodium (400 g), and thereto was sprayed 5% aqueous hydroxypropyl methylcellulose solution previously prepared to be granulated on conditions that intake temperature was 80° C., intake airflow was 7 m³/min, spray liquid flow rate was 200 mL/min and atomizing airflow was 200 L/min. After spraying, the obtained granule was dried on conditions that drying temperature was 80° C. and drying time was 10 minutes, and it was confirmed by a halogen moisture analyzer that the loss on dry was within 2%. The obtained granule powders were sized by using a sizing machine (Fiore F-0 type/manufactured by Tokuju Corporation). Then, the sized granule powders (18000 g) and magnesium stearate (228 g) were blended together by using a blending machine (container size 110 L/manufactured by Furukawa Altec Co., Ltd.) on conditions that rotation rate was 20 rpm and blending time was 5 minutes. The obtained powder mixtures were compressed at a compressing pressure of about 10 kN by using a compression apparatus (CLEANPRESS Correct 12HUK/ manufactured by Kikusui Seisakusho Ltd. for a lurasidone 20, 40 or 80 uncoated tablet, HT-AP12SS-II/manufactured by Hata Iron Works Co., Ltd. for a lurasidone 120 mg uncoated tablet) to prepare a lurasidone 20, 40, 80 or 120 mg uncoated tablet. Then, an uncoated tablet was coated on conditions that temperature for supplying air was 80° C., airflow was 0.6 m³/min, rotation rate of pan was 25 rpm, spray pressure was 0.15 MPa and liquid flow rate was 5 g/min to give a lurasidone 20, 40, 80 or 0.120 mg FC tablet.

(c) Dissolution Test

Manufactured preparations were subjected to the dissolution test according to the Japanese Pharmacopoeia, Dissolution test, Method 2.

Measuring Conditions are Shown Below.

Test solution: Diluted McIlvaine buffer, pH3.8 and 4.0

Paddle rotation: 50 rpm

Test fluid: 900 ml (d) Results

Components of manufactured preparations and results of dissolution tests were shown below.

TABLE 38

| | Components of tablets | | | | |
|---|---|---|---|---|---|
| | | Product name | | | |
| | Lot No. | Lurasidone 20 mg FC tablet 034-15-20 | Lurasidone 40 mg FC tablet 034-15-40 | Lurasidone 80 mg FC tablet 034-15-80 | Lurasidone 120 mg FC tablet 034-15-120 |
| Formulation | Lurasidone | 20 mg | 40 mg | 80 mg | 120 mg |
| | mannitol | 35.5 mg | 71 mg | 142 mg | 216 mg |

TABLE 38-continued

| | 20 mg | 40 mg | 80 mg | 120 mg |
|---|---|---|---|---|
| Partly pregelatinized starch | 20 mg | 40 mg | 80 mg | 120 mg |
| Croscarmellose sodium | 1 mg | 2 mg | 4 mg | 6 mg |
| Hydroxypropyl methylcellulose | 2.5 mg | 5 mg | 10 mg | 15 mg |
| Magnesium stearate | 1 mg | 2 mg | 4 mg | 6 mg |
| Subtotal | 80 mg | 160 mg | 320 mg | 480 mg |
| Hydroxypropyl methylcellulose | 1.001 mg | 1.690 mg | 2.730 mg | 1.100 mg |
| Titanium oxide | 0.308 mg | 0.520 mg | 0.840 mg | 0.825 mg |
| Macrogol 6000 | 0.231 mg | 0.390 mg | 0.630 mg | 5.500 mg |
| Carnauba wax | 0.01 mg | 0.01 mg | 0.01 mg | 0.01 mg |
| Total | 81.55 mg | 162.61 mg | 324.21 mg | 485.51 mg |
| Dissolution profile | | | | |
| Time (min) | Dissolution ratio (%) | | | |
| 10 | 80 | 77 | 77 | 77 |
| 15 | 91 | 90 | 88 | 92 |
| 30 | 100 | 98 | 93 | 96 |
| 45 | 101 | 100 | 94 | 97 |
| pH of test fluid | 4.0 | 4.0 | 4.0 | 3.8 |

As a result, it was confirmed that lurasidone 20, 40, 80 and 120 mg FC tablets manufactured according to the disclosure of the present application showed rapid dissolutions.

<Test 13>

Similarities of dissolution profiles were evaluated for 1 tablet of 40 mg FC tablet/2 tablets of 20 mg FC tablet, 1 tablet of 80 mg FC tablet/2 tablets of 40 mg FC tablet/4 tablets of 20 mg FC tablet, 1 tablet of 120 mg FC tablet/3 tablets of 40 mg FC tablet/6 tablets of 20 mg FC tablet.

(a) Experimental Method

Preparation method and test method were abbreviated because they were similar to dissolution profiles in Test 12.

(b) Results

Dissolution profiles of manufactured preparations and similarities thereof were shown below.

TABLE 39

| | Tablet | | | | | | | |
|---|---|---|---|---|---|---|---|---|
| | 40 mg tablet | 20 mg tablet | 80 mg tablet | 40 mg tablet | 20 mg tablet | 120 mg tablet | 40 mg tablet | 20 mg tablet |
| | Number of tablets | | | | | | | |
| Time (min) | 1 tablet | 2 tablets | 1 tablet | 2 tablets | 4 tablets | 1 tablet | 3 tablets | 6 tablets |
| | Dissolution ratio (%) | | Dissolution ratio (%) | | | Dissolution ratio (%) | | |
| 10 | 77 | 79 | 77 | 78 | 75 | 77 | 90 | 83 |
| 15 | 90 | 90 | 88 | 86 | 84 | 92 | 94 | 90 |
| 30 | 98 | 98 | 93 | 91 | 90 | 96 | 97 | 94 |
| 45 | 100 | 100 | 94 | 93 | 92 | 97 | 98 | 95 |
| f2 value | — | 100 | — | 85 | 74 | — | 88 | 83 |

As a result, it was confirmed that all preparations met the standard of "C. Quality evaluation (2) Similarity of dissolution profiles" in the present specification.

INDUSTRIAL APPLICABILITY

The present invention allows to provide a preparation for oral administration with a good disintegration which comprises as an active ingredient N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptane-dicarboxyimide hydrochloride (lurasidone), which has an equivalent dissolution profile of the active ingredient even though contents of the active ingredient therein are varied.

Figure 1:
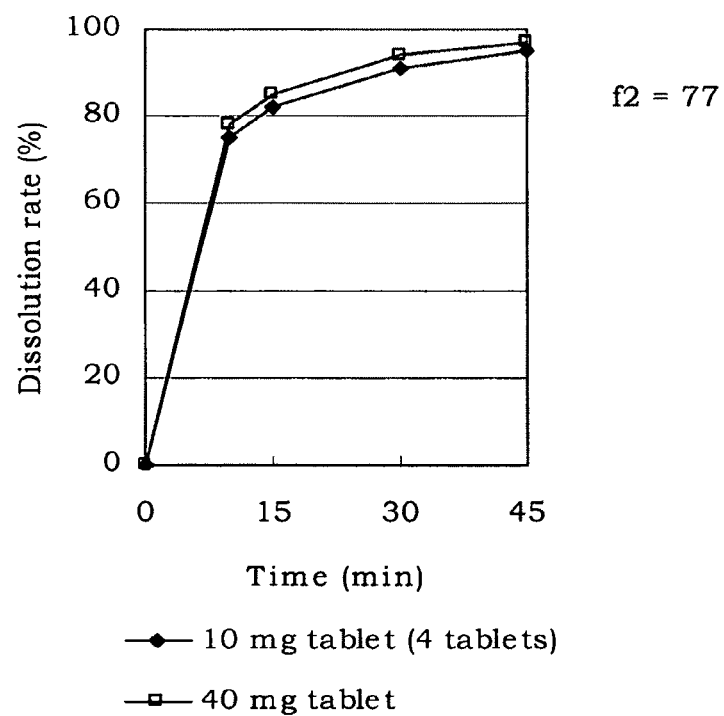
FIG. 1 shows a comparison of dissolution profiles in preparations with different contents of lurasidone. Preparations wherein contents of lurasidone per tablet manufactured according to the art disclosed in Patent Document 2 were 10 mg (4 tablets) and 40 mg (1 tablet) were measured in dissolution profiles.
Figure 2:
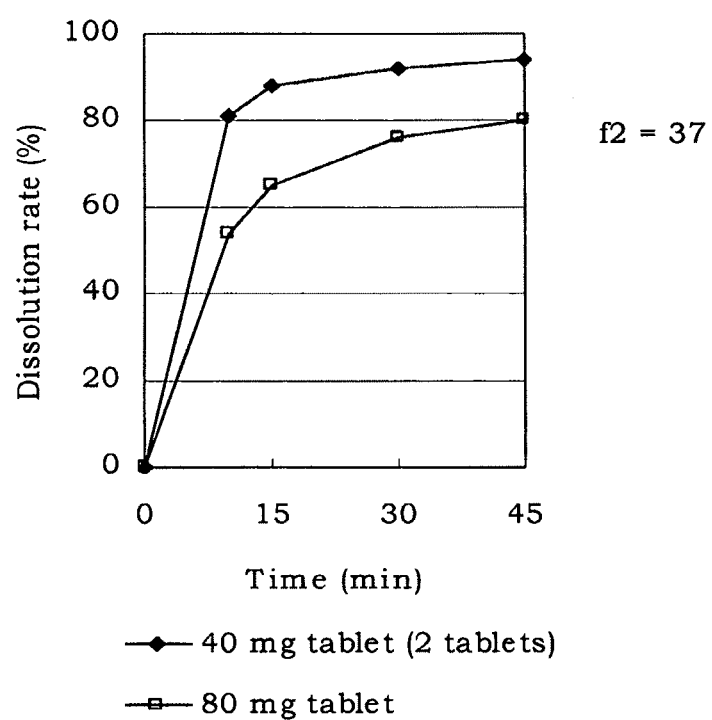
FIG. 2 shows a comparison of dissolution profiles in preparations with different contents of lurasidone. Preparations wherein contents of lurasidone per tablet manufactured according to the art disclosed in Patent Document 2 were 40 mg (2 tablets) and 80 mg (1 tablet) were measured in dissolution profiles.
Figure 3:
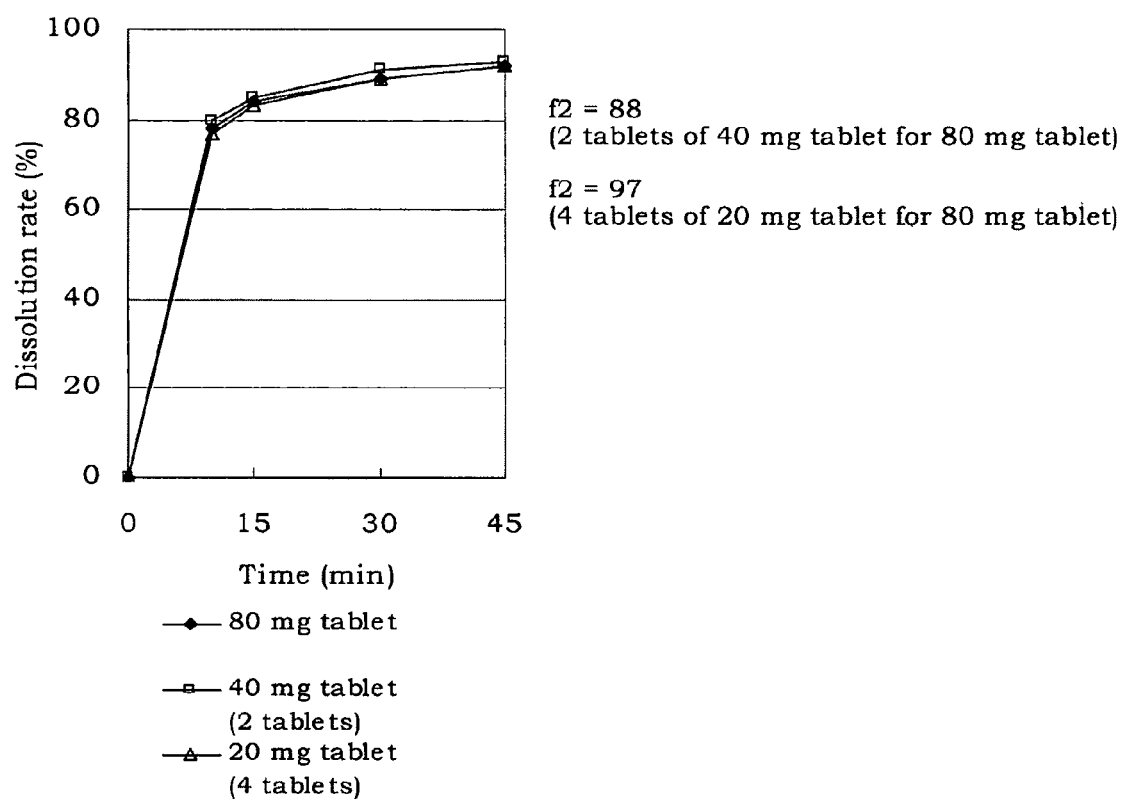
FIG. 3 shows a comparison of dissolution profiles in preparations with different contents of lurasidone. Preparations wherein contents of lurasidone per tablet manufactured according to the present invention were 20 mg (4 tablets), 40 mg (2 tablets) and 80 mg (1 tablet) were measured in dissolution profiles.

The invention claimed is:

1. A tablet for oral administration, comprising:
    from 20 mg to 120 mg of N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptane-dicarboxyimide hydrochloride (lurasidone) as an active ingredient;
    a pregelatinized starch;
    a water-soluble excipient;
    a water-soluble polymer binder; and
    a lubricant,
    wherein the tablet includes lurasidone at a content ratio of 20 to 45% (wt/wt);
    wherein the tablet has a dissolution rate of 80% or more at 30 minutes as measured according to Japanese Pharmacopoeia, Dissolution test, Method 2, where the tablet is subjected to the Dissolution test using paddle rotation at a rotation rate of 50 rpm in 900 mL of a diluted McIlvaine buffer having a pH of 3.8 to 4.0;
    wherein the tablet has a similar dissolution profile to a second tablet comprising from 20 mg to 120 mg of lurasidone,
    wherein similarity of the dissolution profiles is exhibited by the tablet and a second tablet having a similarity factor f2 value of 50 or more,
    wherein the tablet and the second tablet are prepared according to the same method, and comprise the same ratio of lurasidone, pregelatinized starch, water-soluble excipient, water-soluble polymer binder, and lubricant, and
    the second tablet has a different lurasidone content than the tablet.

2. The tablet of claim 1, comprising 20 mg to 40 mg of lurasidone, wherein the second tablet comprises more than 40 mg up to 120 mg of lurasidone.

3. The tablet of claim 1, wherein both the tablet and the second tablet comprise more than 40 mg up to 120 mg of lurasidone.

4. The tablet of claim 1, comprising more than 40 mg up to 120 mg of lurasidone, wherein the second tablet comprises 20 mg to 40 mg of lurasidone.

5. The tablet of claim 1, wherein both the tablet and the second tablet comprise 20 mg to 40 mg of lurasidone.

6. The tablet of claim 1, further comprising a disintegrant.

7. The tablet of claim 6, wherein the disintegrant comprises at least one of corn starch, crystalline cellulose, low substituted hydroxypropylcellulose, carmellose, carmellose calcium, carmellose sodium, croscarmellose sodium, carboxymethyl starch sodium, and crospovidone.

8. The tablet of claim 1, wherein the water-soluble excipient comprises at least one of mannitol and lactose.

9. The tablet of claim 1, wherein the water-soluble polymer binder comprises at least one of hydroxypropyl methylcellulose, polyvinyl alcohol, polyvinylpyrrolidine, and hydroxypropylcellulose.

10. The tablet of claim 1, wherein the lubricant comprises at least one of magnesium stearate, talc, polyethylene glycol, silica, and hydrogenated vegetable oil.

11. The tablet of claim 1, wherein the water-soluble excipient is mannitol, the water-soluble polymer binder is hydroxypropyl methylcellulose, and the lubricant is magnesium stearate.

12. The tablet of claim 6, wherein the disintegrant is croscarmellose sodium, the water-soluble excipient is mannitol, the water-soluble polymer binder is hydroxypropyl methylcellulose, and the lubricant is magnesium stearate.

13. The tablet of claim 1, wherein the pregelatinized starch has a gelatinization ratio of 50% or more.

14. The tablet of claim 1, wherein the dissolution rate is 88% or more.

15. A tablet for oral administration, comprising:
    granules comprising:
        from 20 mg to 120 mg of N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptane-dicarboxyimide hydrochloride (lurasidone) as an active ingredient;
        a pregelatinized starch;
        a water-soluble excipient; and
        a water-soluble polymer binder, and
    a lubricant blended with the granules,
    wherein the tablet includes lurasidone at a content ratio of 20 to 45% (wt/wt);
    wherein the tablet has a dissolution rate of 80% or more at 30 minutes as measured according to Japanese Pharmacopoeia, Dissolution test, Method 2, where the tablet is subjected to the dissolution test using paddle rotation at a rotation rate of 50 rpm in 900 mL of a diluted McIlvaine buffer having a pH of 3.8 to 4.0;
    wherein the tablet has a similar dissolution profile to a second tablet comprising from 20 mg to 120 mg of lurasidone,
    wherein similarity of the dissolution profiles is exhibited by the tablet and a second tablet having a similarity factor f2 value of 50 or more,
    wherein the tablet and the second tablet are prepared according to the same method, and comprise the same ratio of lurasidone, pregelatinized starch, water-soluble excipient, water-soluble polymer binder, and lubricant, and
    the second tablet has a different lurasidone content than the tablet.

16. The tablet of claim 15, comprising 20 mg to 40 mg of lurasidone, wherein the second tablet comprises more than 40 mg up to 120 mg of lurasidone.

17. The tablet of claim 15, wherein both the tablet and the second tablet comprise more than 40 mg up to 120 mg of lurasidone.

18. The tablet of claim 15, comprising more than 40 mg up to 120 mg of lurasidone, C wherein the second tablet comprises 20 mg to 40 mg of lurasidone.

19. The tablet of claim 15, wherein both the tablet and the second tablet comprise 20 mg to 40 mg of lurasidone.

20. The tablet of claim 15, wherein the granules comprise a disintegrant.

21. The tablet of claim 20, wherein the disintegrant comprises at least one of corn starch, crystalline cellulose, low substituted hydroxypropylcellulose, carmellose, carmellose calcium, carmellose sodium, croscarmellose sodium, carboxymethyl stanch sodium, and crospovidone.

22. The tablet of claim 15, wherein the water-soluble excipient comprises at least one of mannitol and lactose.

23. The tablet of claim 15, wherein the water-soluble polymer binder comprises at least one of hydroxypropyl methylcellulose, polyvinyl alcohol, polyvinylpyrrolidine, and hydroxypropylcellulose.

24. The tablet of claim 15, wherein the lubricant comprises at least one of magnesium stearate, talc, polyethylene glycol, silica, and hydrogenated vegetable oil.

25. The tablet of claim 15, wherein the water-soluble excipient is mannitol, the water-soluble polymer binder is hydroxypropyl methylcellulose, and the lubricant is magnesium stearate.

26. The tablet of claim 20, wherein the disintegrant is croscarmellose sodium, the water-soluble excipient is mannitol, the water-soluble polymer binder is hydroxypropyl methylcellulose, and the lubricant is magnesium stearate.

27. The tablet of claim 15, wherein the tablet comprises an uncoated tablet that consists essentially of said granules and lubricant.

28. The tablet of claim 15, wherein the tablet is coated with a film.

29. The tablet of claim 15, wherein the pregelatinized starch has a gelatinization ratio of 50% or more.

30. The tablet of claim 15, wherein the dissolution rate is 88% or more.

* * * * *

UNITED STATES PATENT AND TRADEMARK OFFICE
CERTIFICATE OF CORRECTION

PATENT NO. : 9,907,794 B2  
APPLICATION NO. : 14/733204  
DATED : March 6, 2018  
INVENTOR(S) : Kazuyuki Fujihara Page 1 of 1

It is certified that error appears in the above-identified patent and that said Letters Patent is hereby corrected as shown below:

In the Claims

Column 25, Line 28, "factor 12 value of 50 or more," should read --factor f2 value of 50 or more,--

Column 26, Line 48, "up to 120 mg of lurasidone, C wherein the second tablet" should read --up to 120 mg of lurasidone, wherein the second tablet--

Signed and Sealed this  
Tenth Day of July, 2018

Andrei Iancu  
*Director of the United States Patent and Trademark Office*